United States Patent [19]

Stanley

[11] Patent Number: 5,807,700
[45] Date of Patent: Sep. 15, 1998

[54] **METHOD OF SCREENING ANTI-AMEBIC AGENTS WITH AN *E. COLI* MUTANT HAVING A DELETED ADHE GENE COMPLEMENTED BY THE *E. HISTOLYTICA* EHADH2 GENE**

[75] Inventor: Samuel L. Stanley, Ladue, Mo.

[73] Assignee: Washington University, St. Louis, Mo.

[21] Appl. No.: 562,969

[22] Filed: Nov. 27, 1995

[51] Int. Cl.$^6$ .................................................. C12Q 1/18
[52] U.S. Cl. ..................... 435/32; 435/29; 435/252.3; 435/252.33; 536/23.2; 536/23.7
[58] Field of Search ................ 435/32, 29, 252.3, 435/252.33; 536/23.2, 23.7

[56] References Cited

U.S. PATENT DOCUMENTS

| | | | |
|---|---|---|---|
| 5,130,417 | 7/1992 | Stanley et al. | 530/350 |
| 5,436,138 | 7/1995 | Duronio et al. | 435/69.1 |

OTHER PUBLICATIONS

Olins et al; Gene 73, 227–235 (1988).
Olins & Rangwala, J. Biol. Chem. 264, 16973–16976 (1989).
Yang et al; Mol. Biochem. Parasit. 64, 253–260 (1994).
Studier et al; Methods Enzymol. 185, 60–89 (1990).
Li et al; J. Biol. Chem. 262, 13773–13779 (1987).
Stanley et al; Proc. Natl. Acad. Sci. USA 87, 4976–4980 (1990).
Kessler et al; FEBS Lett. 281, 59–63 (1991).
Yong et al., Proc. Natl. Acad. Sci. USA, vol. 93, pp. 6464–6469, Jun. 1996.
Bruchhaus et al, Biochem J. (Nov. 1, 1994) 303 (Pt3) pp. 743–788.
Maniatis, "Molecular Cloning", (1989) Cold Spring Harbor Laboratory Press, USA, pp. 17.2, 1.85–1.86, 1.33.
Goodlove et al, Gene 85 (1989) pp. 209–214.

*Primary Examiner*—Marian C. Knode
*Assistant Examiner*—Heather A. Bakalyar
*Attorney, Agent, or Firm*—Scott J. Meyer

[57] ABSTRACT

There is disclosed an assay method of screening and identification of anti-amebic drugs which utilizes the ability to inhibit anaerobic growth of a novel bacterial mutant that expresses the EhADH2 gene and which bypasses the conventional need for a parasitic culture. The novel mutant, designated *E. coli*/EhADH2, is cultured under anaerobic conditions, a predetermined or known quantity of the agent to be tested or target compound is combined with the cell culture, and the combination is then monitored to determine the inhibitory effect upon the anaerobic growth of the *E. coli*/EhADH2 cell mutant.

3 Claims, 6 Drawing Sheets

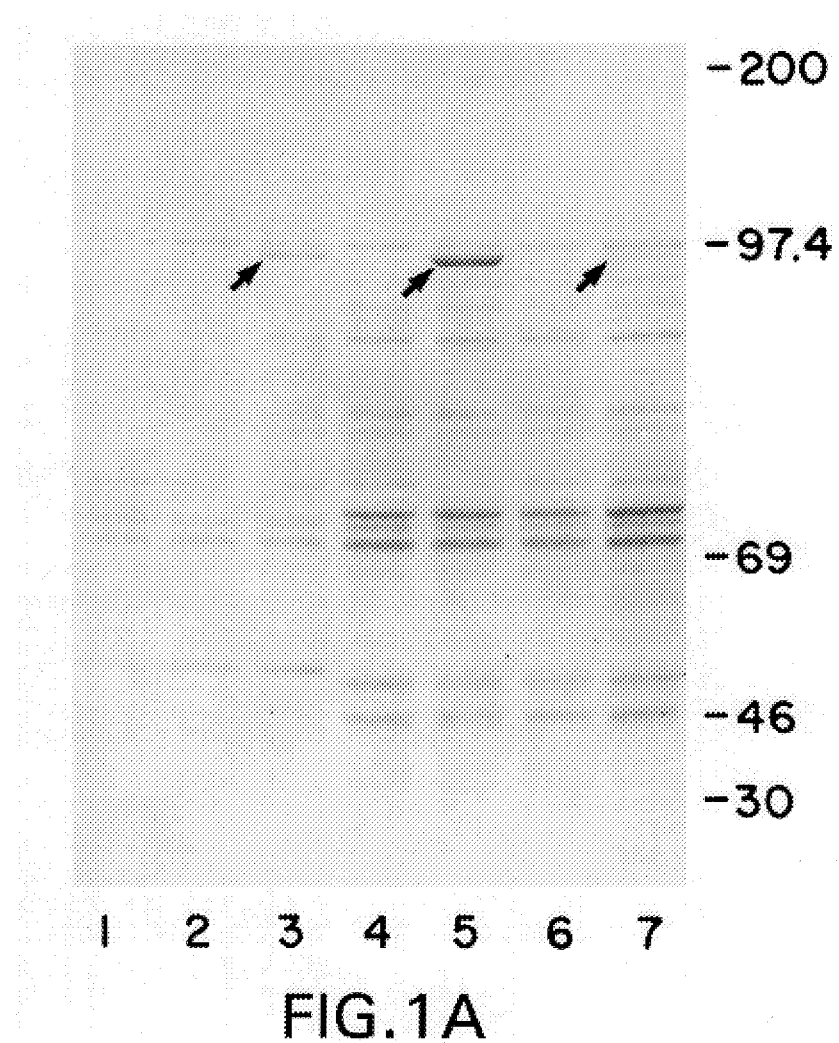

METHOD OF SCREENING ANTI-AMEBIC AGENTS WITH AN *E. COLI* MUTANT HAVING A DELETED ADHE GENE COMPLEMENTED BY THE *E. HISTOLYTICA* EHADH2 GENE

BACKGROUND OF THE INVENTION

This invention relates to a novel method of screening and identification of anti-amebic drugs. More particularly, the invention relates to an assay that utilizes the ability to inhibit anaerobic growth of a novel bacterial mutant for identifying therapeutic agents effective against parasitic diseases and which thereby bypasses the conventional need for a parasitic culture.

(Note: Literature references on the following background information and on conventional test methods and laboratory procedures well known to the ordinary person skilled in the art, and other such state-of-the-art techniques as used herein, are indicated in parentheses, and appended at the end of the specification.)

The intestinal protozoan parasite *Entamoeba histolytica* (*E. histolytica*) causes amebic dysentery and amebic liver abscess, which are associated with significant morbidity and mortality worldwide. Amebiasis is currently treated with the drug metronidazole which remains an effective agent in most cases. However, side effects associated with metronidazole (1,2), and the growing problem of metronidazole resistance among other protozoan parasites such as *Trichomonas vaginalis* (3–5) and *Giardia lamblia* (6,7), has fueled interest in developing new anti-amebic agents.

*E. histolytica* is an anaerobic eukaryote which lacks mitochondria, and ferments glucose to acetaldehyde and alcohol with pyruvate and acetyl-CoA as intermediates (8,9). Recently, a potential target for anti-amebic chemotherapy was identified in the (*E. histolytica*) alcohol dehydrogenase/acetaldehyde dehydrogenase (EhADH2) molecule (10). EhADH2 is a bifunctional AND$^+$-linked enzyme with both alcohol dehydrogenase (ADH) and acetaldehyde dehydrogenase (ALDH) activity, and is believed to be responsible for catalyzing two key steps in the *E. histolytica* fermentation pathway (9–11).

Because of the critical role of EhADH2 in the amebic fermentation pathway, and the lack of known eukaryotic homologues of the EhADH2 enzyme, EhADH2 represents a potential target for anti-amebic chemotherapy. However, screening of compounds for anti-amebic activity is hampered by the cost of large scale growth of *E. histolytica* and difficulties in quantitating drug efficacy in vitro by the cumbersome methods for measuring growth inhibition by counting viable trophozoites.

Accordingly, a method for the screening and identification of anti-amebic drugs which does not depend on the need for a parasitic culture would have substantial use in the pharmaceutical industry.

BRIEF DESCRIPTION OF THE INVENTION

In accordance with the present invention, a rapid assay is provided for screening and identifying compounds with anti-EhADH2 activity. The assay utilizes the ability of the target compounds to inhibit anaerobic growth of a novel bacterial mutant that expresses the EhADH2 gene.

EhADH2 is a bifunctional gene that encodes an *E. histolytica* alcohol dehydrogenase (ADH) and acetaldehyde dehydrogenase (ALDH). The EhADH2 cDNA clone has an open reading frame of 2610 nucleotides encoding a 870-amino acid peptide with a predicted mol. wt. of 95,758 Daltons (10). It has about 48% amino acid homology with the multifunctional enzyme encoded by the *E. coli* adhE gene (10).

As used herein, the EhADH2 gene is expressed in a novel mutant strain of *E. coli* carrying a deletion of the adhE gene (ΔadhE). Said mutant strain is designated herein as *E. coli*/EhADH2. Expression of the functional EhADH2 protein in *E. coli*, restores the ability of the mutant *E. coli* strain to grow under anaerobic conditions. That is, by using a plasmid containing the EhADH2 cDNA to complement an *E. coli* strain with an engineered deletion of the adhE gene, a mutant *E. coli* is produced that requires the *E. histolytica* enzyme for anaerobic growth.

Suitable expression vectors for expression of EhADH2 in *E. coli* are illustratively constructed from the conventional T7 promoter based vector pET3a and recA promoter based vector pMON2670. The pET3 vectors contain a T7 promoter inserted into the BamHI site of the multicopy plasmid pBR322 in the orientation that transcription is directed counterclockwise, opposite to that from the tet promoter. In pET3a, the GGA triplet of the BamHI site is in the open reading frame (18). The pET3a vector also is commercially available from Novagen, Madison, Wis.

The recA promoter-based vector pMON2670 is described in U.S. Pat. No. 5,436,138 and is available without restriction from the American Type Culture Collection, Rockville, Md., under accession number ATCC 68218.

This plasmid is based on pMON5515 described by Olins et al., Gene 73, 227–235 (1988). It has an ampicillin resistance marker (AMP$^r$) and ColE1 replicon (ori-ColE1), the nalidixic acid-inducible *E. coli* recA promoter and the g10-L ribosome binding site.

In addition, pMON2670 carries a T7 transcription terminator (T7 ter).

This plasmid also contains an irrelevant coding region, namely a portion of the human proANF gene (atrial natriuretic factor, atriopeptigen) downstream of the g10-L ribosome binding site.

Unique NcoI, NdeI and HindIII restriction sites permit the simple removal of the irrelevant coding region.

The assay method of the invention thus comprises identifying anti-amebic compounds having anti-EhADH2 activity by screening the target compounds for the ability to inhibit the anaerobic growth of the *E. coli*/EhADH2 strain. That is, the *E. coli*/EhADH2 cell mutant is cultured under anaerobic cell culture conditions, a pre-determined or known quantity of the agent to be tested or target compound is combined with the cell culture, and the combination is then monitored to determine the inhibitory effect upon the anaerobic growth of the *E. coli*/EhADH2 cell mutant.

Conventional cell culture media for the maintenance and propagation of *E. coli*, e.g., M9 minimal medium agar, can be used for the anaerobic cell culture conditions.

In a preferred embodiment of the invention, the inhibition of anaerobic bacterial growth is monitored or quantitated by measuring the optical density (O.D.) of the cell culture at 600 nm following a predetermined period of time after inoculation with the target compound, e.g., at 24 and/or 48 hours after inoculation. The effect of the target compound on the resulting cell growth is measured as a change in the turbidity of the cell culture.

Since the EhADH2 is a AND$^+$-dependent bifunctional enzyme with alcohol dehydrogenase (ADH) and acetaldehyde dehydrogenase (ALDH) activities which also uses Fe$^{2+}$ as a cofactor, the ADH and ALDH activities of the culture supernatant can also be readily determined spectrophotometrically by measuring the decrease in absorbance at 340 nm following oxidation of NADH to AND. This is based on the fact that reduced nicotinamide adenine dinucleotide (NADH) absorbs light with a peak at 340 nm, while the oxidized form (AND) shows no absorption between 300 and 400 nm.

Target compounds that are capable of inhibiting anaerobic growth, but not aerobic growth of the E. coli/EhADH2 strain in the method of assay defined herein, are useful inhibitors of EhADH2 activity and, therefore, potential therapeutic agents effective against parasitic diseases.

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments of the invention taken in conjunction with the appended drawings in which:

BRIEF DESCRIPTION OF THE DRAWINGS

FIGS. 1A and 1B show Expression of EhADH2 by E. coli. FIG. 1A shows Coomassie blue staining of SDS-PAGE separated lysates from:

Lane 1, BL21(DE3);
Lane 2, BL21(DE3)/pET3a;
Lane 3, BL21(DE3)/pET/EhADH2;
Lane 4, SHH31;
Lane 5, SHH31(DE3)/pET/EhADH2;
Lane 6, SHH31/pMON2670;
Lane 7, SHH31/pMON/EhADH2.

A band at 96 kDa (arrow) is seen in lysates from strains expressing EhADH2 (lanes 3,5,7) and not from control strains.

Figure 1B:
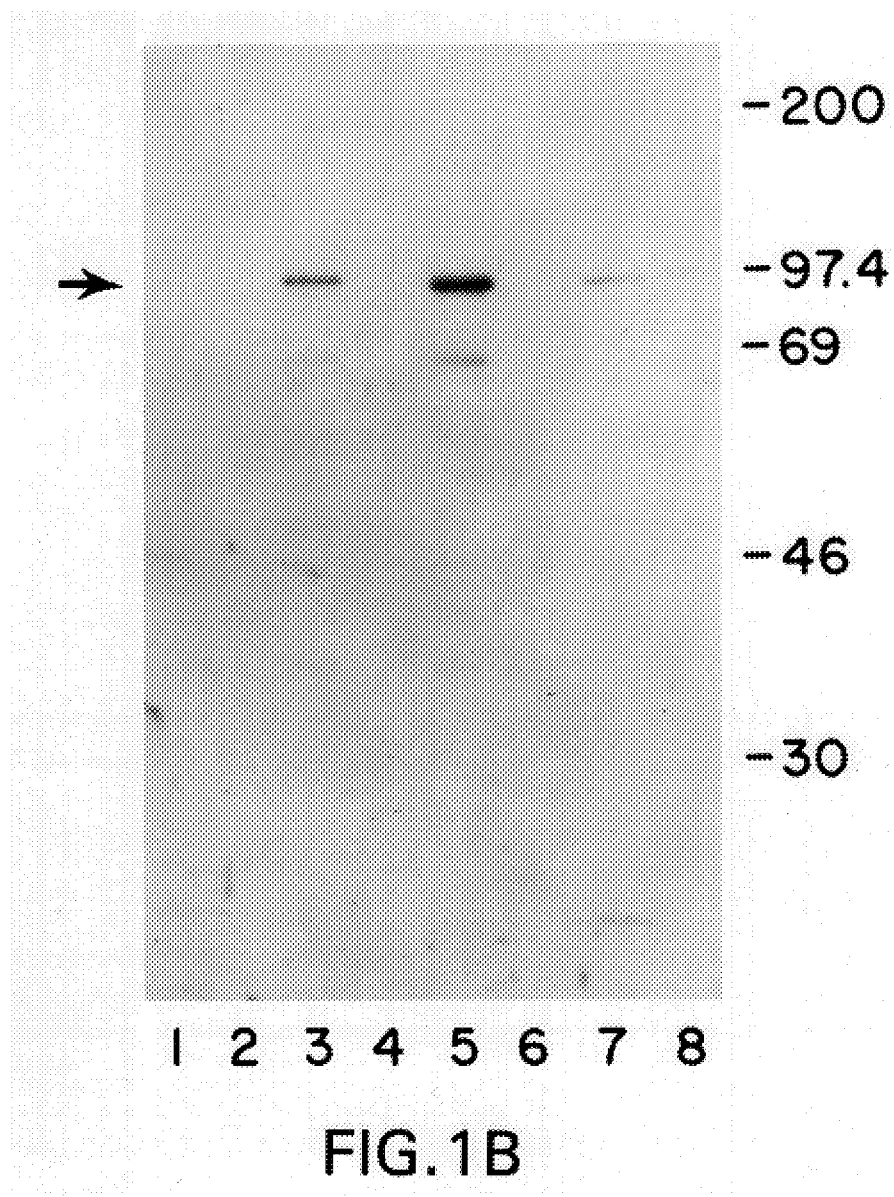

FIG. 1B shows immunoblotting of lysates with anti-EhADH2 serum. Lane assignments are identical to FIG. 1A; Lane 8 is lysates from E. histolytica HM1:IMSS. A species at 96 kDa is detected in E. coli lysates expressing EhADH2 (lanes 3,5,7) and in E. histolytica (lane 8). Molecular weight standards (in kDa) are indicated at the right of each of FIGS. 1A and 1B.

Figure 2:
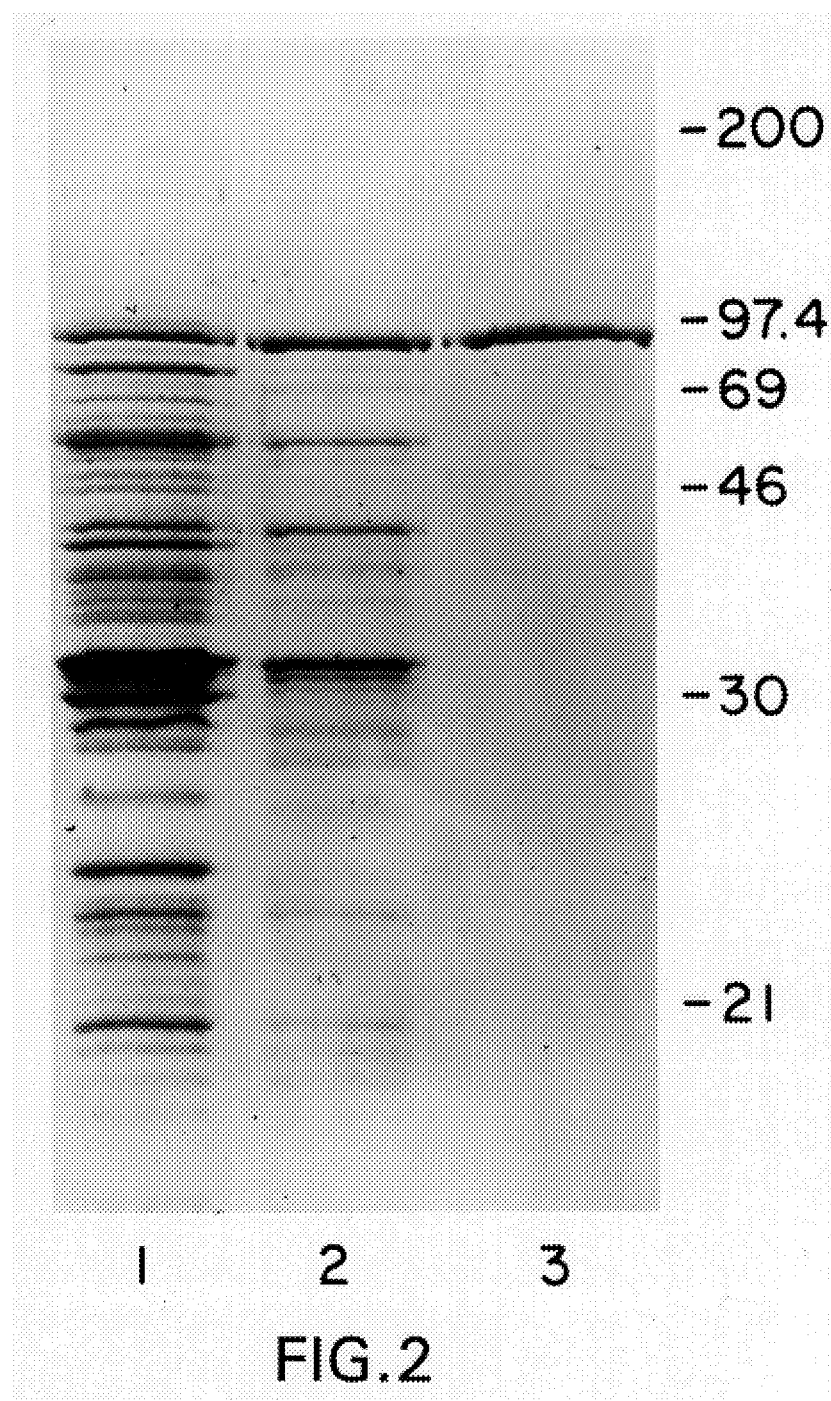

FIG. 2 shows purification of recombinant EhADH2. Coomassie blue staining is shown for SDS-PAGE separated samples of:

Lane 1, lysate of SHH31(DE3)/pET/EhADH2;
Lane 2, 35% ammonium sulfate precipitate fraction of lysates from lane 1;
Lane 3, fraction containing EhADH2 obtained from the gel filtration of ammonium sulfate precipitated lysates (lane 2) on a column of SEPHAROSE CL-6B Gel Filtration Media.

Figure 3:
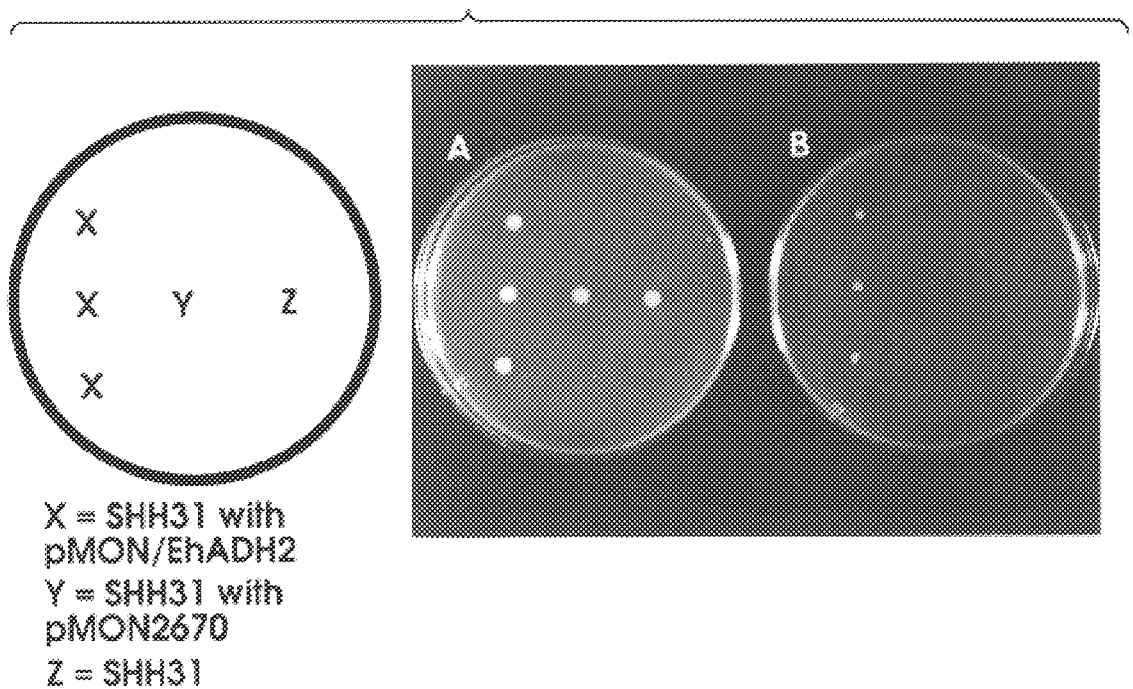

FIG. 3 shows complementation of E. coli ΔadhE strain SHH31 by expression of EhADH2.

Under aerobic conditions (culture A), all E. coli strains grow.

Under anaerobic conditions (culture B), SHH31 expressing EhADH2 (SHH31/pMON/EhADH2) can grow (colonies indicated by "X"), but SHH31 transformed with the pMON2670 vector alone (colonies marked by "Y"), or untransformed SHH31 (colonies marked "Z"), show no growth.

Figure 4:
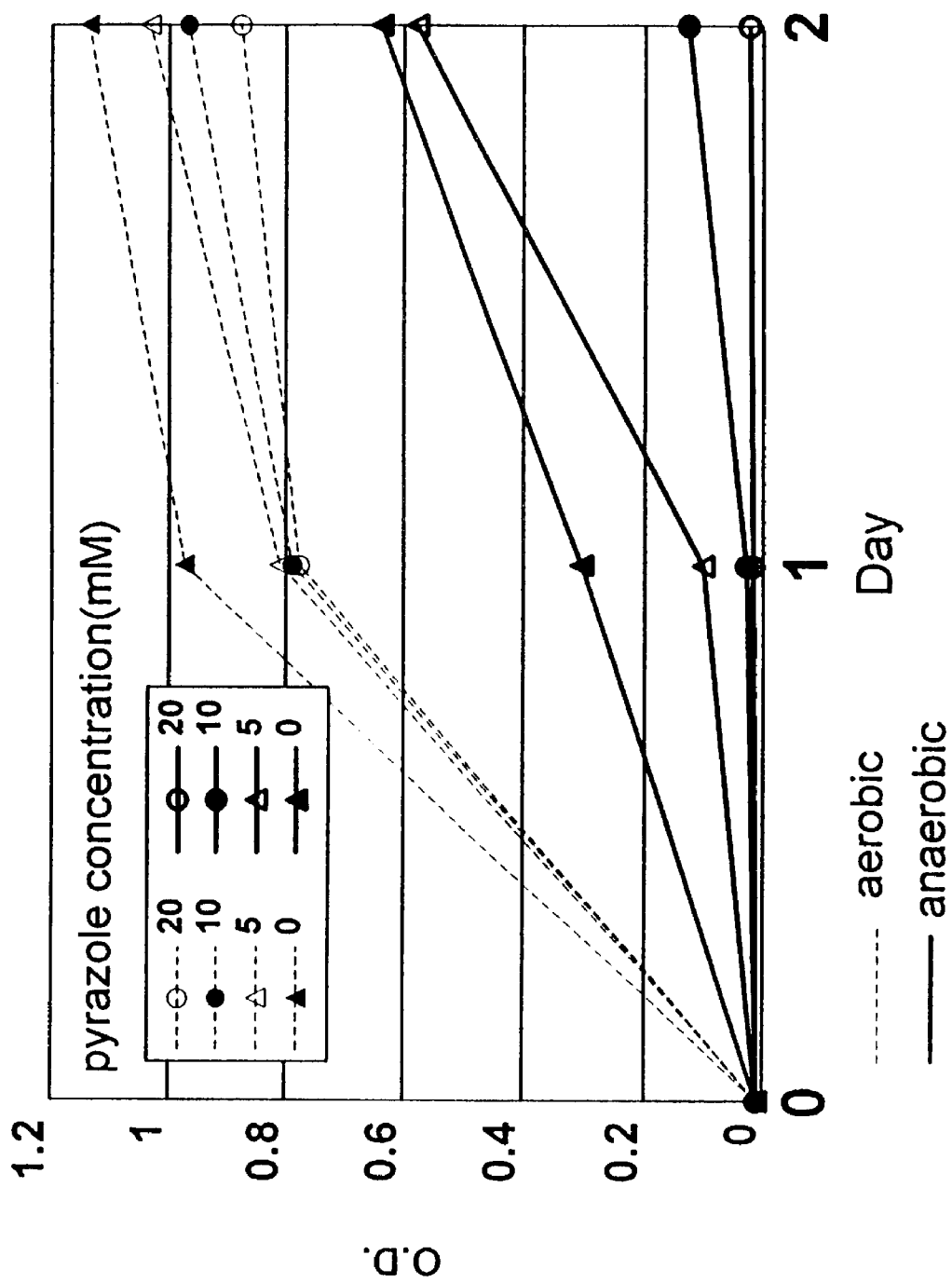

FIG. 4 is a graphical representation which shows inhibition on the anaerobic growth of ΔadhE mutant E. coli complemented with EhADH2 by pyrazole. SHH31/pMON/EhADH2 was inoculated on the M9 minimal liquid media containing pyrazole at the indicated concentrations (mM), and incubated aerobically (dotted lines) or anaerobically (solid lines) for two days. Optical densities (O.D.) at 600 nm were read at 1 and 2 days post-inoculation to assess the growth of the bacteria.

Figure 5:
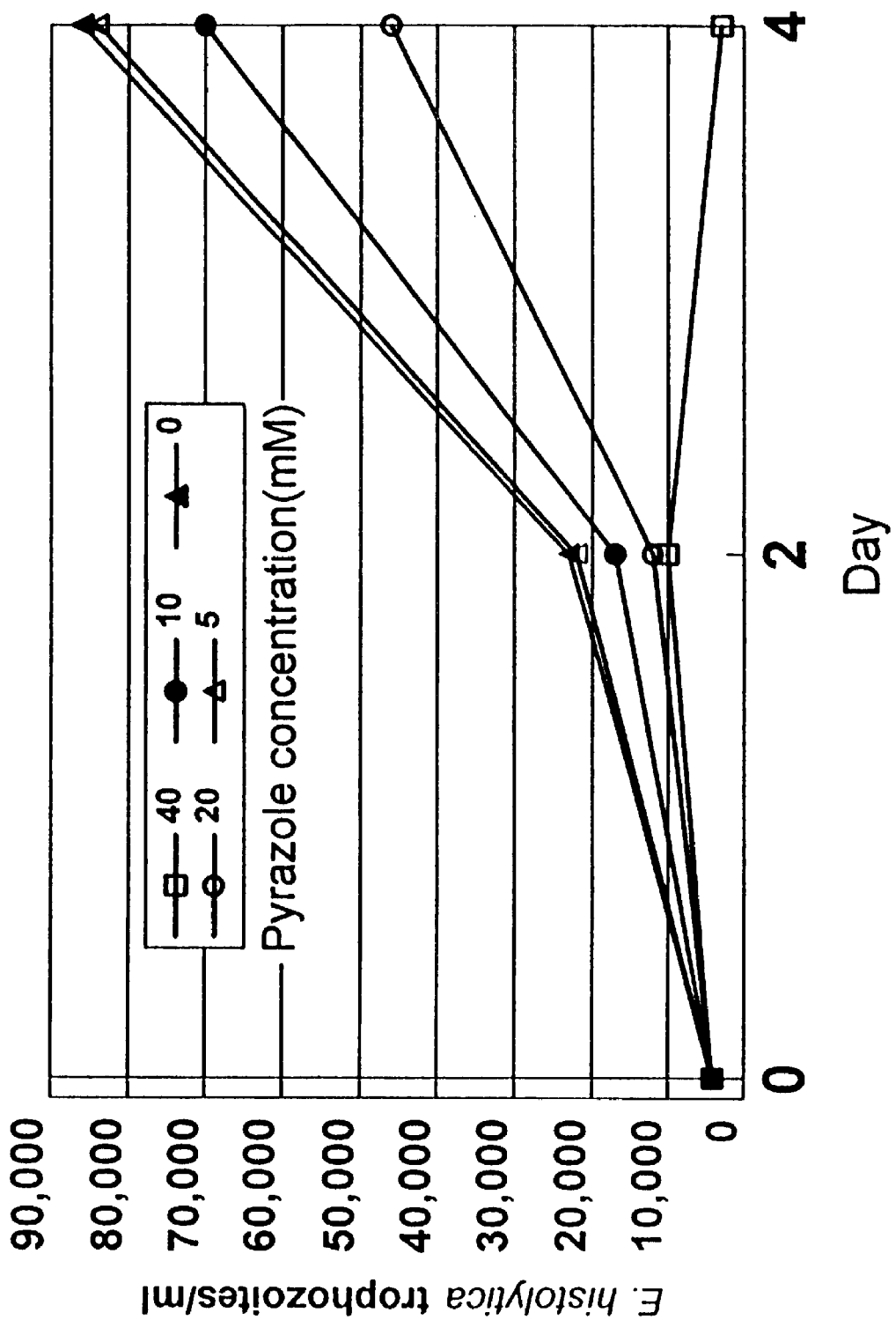

FIG. 5 is a graphical representation which shows pyrazole inhibits E. histolytica growth. Culture tubes containing E. histolytica HM1:IMSS trophozoites with an inoculation dose of $4 \times 10^3$/tube were incubated for four days with pyrazole in concentrations ranging from 5 to 40 mM. The number of viable amebic trophozoites (E. histolytica trophozoites/ml) at 2 and 4 days post-inoculation is indicated.

The EhADH2 molecule is a bifunctional $AND^+/Fe^{2+}$-dependent enzyme with both ADH and ALDH activities (10,11).

It appears to be a critical enzyme in the amebic glucose to ethanol pathway, catalyzing two reactions (acetyl-CoA to acetaldehyde and acetaldehyde to ethanol) in fermentation (8,9).

The EhADH2 molecule is homologous to certain enzymes present in facultatively or obligate anaerobic bacteria (12–14).

The prototype of these enzymes is the E. coli AdhE molecule, an $AND^+$-dependent enzyme which also uses $Fe^{2+}$ as a cofactor, and possesses ADH, ALDH, and pyruvate-formate-lyase deactivase activities (12–21).

The AdhE enzyme is required for anaerobic growth of E. coli, and expression of this gene is induced by anaerobic conditions (24).

In addition to its critical role in the amebic fermentation pathway, the EhADH2 molecule may serve other functions in E. histolytica as well.

The EhADH2 protein was originally isolated because of its ability to bind extracellular matrix proteins such as laminin and fibronectin (10), and it has been recently shown that the EhADH2 molecule, or an isoform, is shed or secreted by amebic trophozoites (25).

The assay method of the invention is based on the successful expression of a functional EhADH2 molecule in E. coli. The initial approach was to express EhADH2 as either a GST- or 6His-fusion protein. However, in both cases while a fusion protein was successfully expressed, it had no enzymatic activity.

This contrasts with the findings for the $NADP^+$-dependent ADH of E. histolytica (EhADH1), which retained ADH activity as a GST-fusion protein (26).

This difference may reflect a requirement for multimer formation for EhADH2 activity which could not be achieved by fusion proteins.

Both the native EhADH2 enzyme and the homologous E. coli AdhE enzyme form multimers that array into helical structures of up to 100 nm (when viewed by electron microscopy) called spirosomes (11,21).

The functional recombinant EhADH2 enzyme that was produced in E. coli had a molecular mass of greater than 200 kDa by gel filtration, consistent with multimer formation. The purified recombinant enzyme was used to look at the substrate specificity of EhADH2.

The $K_m$ values for ethanol, $AND^+$, NADH, and acetyl-Co-A were comparable to those obtained for the native enzyme (11), while values for acetaldehyde were somewhat higher than those seen with the native enzyme.

It was demonstrated that in addition to ethanol, the primary alcohols butanol and propanol are substrates for EhADH2, but methanol, retinol, isopropanol and sec-butanol are not.

The substrate specificity of the ADH portion of EhADH2 clearly differs from the NADP+-dependent EhADH1 which preferentially utilizes branch-chained alcohols (26).

No structural homologue to the full length EhADH2 has yet been found among eukaryotic ADH or ALDH enzymes, although there are eukaryotic ALDH enzymes with some homology to the N-terminal (ALDH) domains of EhADH2 and related prokaryotic molecules (13).

The unique structure of the EhADH2 molecule among eukaryotic ADH molecules and its critical role in the amebic fermentation pathway make it an ideal target for anti-amebic chemotherapy.

However, the cost of growing E. histolytica in culture, and the cumbersome methods for measuring growth inhibition (counting viable trophozoites), make large-scale screening of compounds for anti-amebic activity difficult.

To solve this problem, a screening system was developed for compounds with anti-EhADH2 activity which utilizes inhibition of anaerobic bacterial growth (easily quantitated by measuring the O.D. of liquid bacterial cultures) to identify effective compounds.

An E. coli strain was produced that requires EhADH2 activity to grow under anaerobic conditions by using the EhADH2 gene to complement a mutant strain of E. coli containing an engineered deletion in the adhE gene. Compounds capable of inhibiting anaerobic, but not aerobic growth of this strain, are potential specific inhibitors of EhADH2 activity.

The feasibility of this approach was tested using the compound pyrazole, which is known to inhibit AND+-dependent ADH enzymes. Pyrazole inhibited anaerobic but not aerobic growth of the E. coli SHH31/pMON/EhADH2 strain, and consistent with this finding, pyrazole was shown to inhibit both E. histolytica trophozoite growth and the purified recombinant EhADH2 enzyme at similar concentrations, indicating the effects of pyrazole on E. coli anaerobic growth and E. histolytica growth were based on inhibition of EhADH2.

In this regard, while the NADP+-dependent EhADH1 molecule is also inhibited by pyrazole (26), the $K_i$ for pyrazole and EhADH1 is 1.4 $\mu$M, a concentration range where pyrazole had no effect on E. histolytica growth. Thus, while pyrazole does not represent an ideal candidate for a specific EhADH2 inhibitor, its use in this screening assay demonstrates that this approach can identify compounds with anti-EhADH2 activity.

The growth requirements and complex life cycles of a number of parasites can make the identification of new anti-parasitic drugs and susceptibility testing of existing compounds difficult and costly endeavors. In addition, genetic systems which allow targeted mutations are poorly developed or non-existent for a number of protozoan and helminthic parasites.

The assay method of the invention for rapidly identifying specific inhibitors of the parasitic enzyme takes advantage of the presence of homologous genes in E. coli and the parasite E. histolytica which encode an enzyme required for a selectable function (the ability to grow anaerobically):

the ability to generate bacteria with mutations of that gene, and the ability to complement that mutation with the parasitic gene.

The use of bacteria to bypass the need for parasite culture in the initial screening process for anti-parasitic agents can greatly simplify and reduce the cost of identifying new therapeutic agents effective against parasitic diseases.

In order to illustrate the invention in further detail, the following specific laboratory examples were carried out with the results indicated. Although specific examples are thus illustrated, it will be understood that the invention is not limited to these specific examples or the details therein.

EXAMPLES

Materials and Methods

E. coli and E. histolytica strains and culture conditions. Conventional E. coli strains, DH5α, BL21(DE3), and SHH31 (Δadh zch::Tn10 fadR met tyrT) (15) were used for transformation and the expression of recombinant EhADH2. Aerobic cultures were grown in LB medium with agitation at 37° C. For anaerobic growth, bacteria were incubated in anaerobic jars, BBL®GasPak® System under an $H_2$-$CO_2$ atmosphere generated by BBL GAS PAK Anaerobic System Envelopes (Becton Dickinson, Cockeysville, Md.).

Anaerobic indicator strips were used to ensure anaerobic conditions. M9 minimal medium used for anaerobic growth was supplemented with glucose at 0.25%, thiamine (1 mM), $CaCl_2$(0.1 mM), $MgSO_4$(1.2 mM), and the following trace minerals: Fe(50 $\mu$M), Se(5 $\mu$M), Mo(5 $\mu$M), Mn(5 $\mu$M) (16).

Anaerobic liquid cultures were grown without agitation in tubes inside the anaerobic jars at 37° C. Solid media contained 1.5% Bacto Agar (Difco, Detroit, Mich.). Trophozoites of E. histolytica HM1:IMSS were cultured axenically in BYI-S-33 medium by conventional procedure as previously described (17).

Construction of the EhADH2 Expression Vectors

Two expression vectors were employed for prokaryotic expression of EhADH2, the T7 promoter-based vector pET3a (Novagen, Madison, Wis.) (18), and the recA promoter-based vector pMON2670 (19). As used herein, pET refers to pET3a, and pMON refers to pMON2670.

The sequences flanking the EhADH2 coding region were modified by the incorporation of a BamHI site next to the termination codon TAA at the 3' end of EhADH2, and a NcoI site at the initiating ATG codon using PCR with the EhADH2 cDNA as the template (10).

The EhADH2 sequence was then ligated in frame into NcoI and BamHI digested pET3a as two fragments, NcoI/PstI and PstI/BamHI to construct the expression vector pET/EhADH2. To construct pMON/EhADH2, the coding sequences were ligated in frame into NcoI/SacI digested pMON2670 as two fragments, NcoI/PstI and PstI/SacI.

Expression of Recombinant EhADH2 in E. Coli SHH31 (ΔadhE)

EhADH2 was first expressed in E. coli SHH31 using the pMON/EhADH2 vector. Subsequently, the SHH31 strain was lysogenized by λDE3 using a lysogenization kit (Novagen) according to the manufacturers product protocol. EhADH2 was then expressed in SHH31 (DE3) using the pET/EhADH2 vector. SDS-PAGE analysis of bacterial lysates for expression of recombinant EhADH2 was performed by conventional methods as previously described (20).

Western blotting was performed using a 1:500 dilution of rabbit antiserum raised to a recombinant 6His-EhADH2 fusion protein using previously described conventional methods (20). Complementation of the ΔadhE mutation by EhADH2 was tested by measuring the anaerobic growth of E. coli SHH31 transformed with pMON/EhADH2 on minimal glucose media compared with that of E. coli SHH31 transformed with pMON2670.

Assay of Alcohol Dehydrogenase (ADH) and Acetaldehyde Dehydrogenase (ALDH) Activity of Bacterial Lysates and Purified Recombinant EhADH2.

ADH activity of the supernatant fraction from bacterial lysates, or of the purified recombinant enzyme was assayed spectrophotometrically by measuring the decrease in absorbance at 340 nm following the oxidation of NADH to AND (21). The cuvette contained 6 mM DTT, 5 mM $MgSO_4$, 0.1 mM $Fe(NH_4)_2(SO_4)_2$, 0.4 mM NADH, 10 mM acetaldehyde, and 0.1 M MOPS-KOH buffer (pH 7.5) to give a final volume of 1.0 ml. MOPS=3–[N-Morpholino] propanesulfonic acid; DTT=dithiothreitol.

ALDH activity was assayed using the same method, with the substitution of 0.1 mM acetyl-CoA for acetaldehyde in the reaction buffer. A unit of enzyme activity is defined as the micromoles of product formed per min of incubation at room temperature.

To study the substrate specificity and kinetics of the purified recombinant EhADH2 molecule, the spectrophotometric assay of ADH activity was again utilized, with 5 μg of the purified enzyme in the presence of 50 mM glycine/NaOH buffer (pH 9.5) containing 6 mM DTT, 5 mM $MgSO_4$, 0.1 mM $Fe(NH_4)_2(SO_4)_2$, 1 mM $AND^+$, and varying concentrations of the substrate alcohol to be tested (11). The $K_m$ and $K_{cat}$ values expressed were determined using non-linear regression to fit the values for initial velocity and substrate concentration to the Michaelis-Menten equation.

Purification of recombinant EhADH2

A one-liter culture of *E. coli* SHH31(DE3) carrying pET/EhADH2 was grown overnight under aerobic conditions. The bacteria were collected by low speed centrifugation, resuspended in 20 mM MOPS-KOH buffer (pH 7.5), disrupted by sonication, and sedimented by centrifugation at 150,000 g for 1 h at 4° C.

The supernatant was brought to 35% saturation with solid ammonium sulfate and stirred for 1 hr at 4° C. The suspension was centrifuged at 15,000 g for 20 min at 4° C.

The supernatant was dialyzed extensively against 20 mM MOPS-KOH (pH 7.5), and chromatographed over a 1.6 cm×90 cm Sepharose® CL-6B (Sigma, St. Louis, Mo.) gel filtration column equilibrated with 20 mM MOPS-KOH buffer. Using a flow rate of 0.4 ml/min, fractions were collected and screened for $AND^+$ dependent ADH activity.

EhADH2 Inhibition Assay

*E. coli* SHH31 transformed with pMON/EhADH2 were inoculated into M9 minimal liquid medium and grown under anaerobic or aerobic conditions in the presence or absence of pyrazole (Sigma Chemical Co., St. Louis, Mo.) at concentrations of 5 to 20 mM. Growth was monitored by determining the optical density (O.D.) at 600 nm at 24 and 48 hrs post-inoculation. To study inhibition of *E. histolytica* growth, standard culture tubes containing an initial inoculation of 4×10³/tube *E. histolytica* HM1:IMSS trophozoites were incubated for four days in the presence or absence of pyrazole at concentrations of 5 to 40 mM. Viable trophozoites were counted using a hemacytometer at days 2 and 4, and the number of trophozoites/ml recorded.

RESULTS

Expression of Functional EhADH2 in *E. Coli*

Nucleotides 3 through 2,620, representing the entire coding region of the EhADH2 cDNA clone, were first expressed as glutathione-S-transferase (GST) and 6His-EhADH2 fusion proteins, using the pGEX-KG (22), and pQE (Qiagen, Chatsworth, Calif.) vectors, respectively. However, neither recombinant fusion protein possessed detectable ADH or ALDH activity.

The 6His-EhADH2 recombinant protein was purified and used to generate a specific anti-EhADH2 antiserum. The EhADH2 protein was expressed without a fusion partner using the pET/EhADH2 construct as described in "Materials and Methods". As shown in FIG. 1A, *E. coli* BL21(DE3) containing the pET/EhADH2 plasmid produced a protein at 96 kDa (the predicted size of the EhADH2 protein) (lane 3), while *E. coli* BL21(DE3) transformed with the pET3a vector alone did not show a species at 96 kDa (lane 1).

To confirm that the species at 96 kDa was EhADH2, Western blotting of the SDS-PAGE separated bacterial lysates with antiserum to the 6His-EhADH2 recombinant protein was performed. Anti-EhADH2 antiserum bound to the species at 96 kDa in lysates from BL21(DE3) expressing pET/EhADH2 (FIG. 1B, lane 3), but not in control lysates of BL21(DE3) transformed with the pET vector alone (FIG. 1B, lane 1).

The ADH and ALDH activity of the recombinant EhADH2 protein was first assessed by measuring the enzymatic activity of lysates obtained from aerobically grown *E. coli* expressing the pET/EhADH2 plasmid, and *E. coli* BL21(DE3) containing the pET vector alone. As shown in Table 1 below, lysates from pET/EhADH2-transformed bacteria expressing the 96 kDa EhADH2 enzyme, had high levels of ADH and ALDH activity when compared to lysates from control *E. coli* BL21(DE3) containing the pET vector alone.

EhADH2 Can Complement (ΔadhE) in *E. coli* SHH31

In order to determine whether the EhADH2 gene product would complement the *E. coli* adhE gene, EhADH2 was expressed in *E. coli* SHH31 (ΔadhE) (15). This strain produces no AdhE enzyme, and is unable to grow in M9/glucose minimal media under anaerobic conditions (15).

As shown in FIG. 3, *E. coli* SHH31 transformed with pMON/EhADH2 was able to grow on M9 minimal medium agar under both aerobic and anaerobic conditions, while *E. coli* SHH31 transformed with pMON alone could only grow under aerobic conditions. Thus, the product of the amebic EhADH2 gene can complement the *E. coli* (ΔadhE) mutation.

It was confirmed that SHH31 was producing the EhADH2 protein by examining bacterial lysates from both SHH31 transformed with pMON/EhADH2 and lysogenized SHH31 (DE3) expressing the pET/EhADH2 vector. As shown in FIG. 1A, expression of EhADH2 was detected in SHH31/pMON/EhADH2 (lane 7), and SHH31(DE3)/pET/EhADH2 vector (lane 5).

The identity of the 96 kDa species as EhADH2 was confirmed by Western blotting using anti-EhADH2 antiserum (FIG. 1B, lanes 5 and 7). Lysates obtained from both SHH31(DE3) transformed with pET/EhADH2 and SHH31 transformed with pMON/EhADH2 contained detectable ADH and ALDH activity (Table 1) while lysates from the parent strains showed no detectable ADH or ALDH activity.

Purification and Determination of the Substrate Specificity of Recombinant EhADH2

By expressing EhADH2 in *E. coli* SHH31, a source of recombinant EhADH2 was obtained without any possible contamination by the bacterial AdhE enzyme. Because greater ADH and ALDH activity was detected in lysates from SHH31(DE3)/pET/EhADH2 (Table 1), this system was utilized for purification of recombinant EhADH2.

Purification of recombinant EhADH2 from lysates of pET/EhADH2 transformed *E. coli* SHH31(DE3) was accomplished using ammonium sulfate precipitation and gel filtration on Sepharose® CL-6B (FIG. 2). Purity was assessed using Coomassie staining of SDS-PAGE separated fractions (FIG. 2) and measuring ADH activity.

The purified recombinant EhADH2 retained both ADH and ALDH activity (Table 2). Based on gel filtration, the molecular mass for the recombinant EhADH2 enzyme was greater than 200 kDa; a similar pattern was seen with the purification of the native E. histolytica enzyme (11), and suggests the recombinant enzyme forms multimers similar to those seen with the E. coli AdhE protein and native EhADH2 (11).

The purified recombinant enzyme was used to study the substrate specificity of EhADH2. It was found that only the primary alcohols ethanol, 1-propanol, and butanol, were substrates for the enzyme (Table 2). No reactivity with isopropanol or sec-butanol was detected, and neither retinol nor methanol were substrates for the enzyme.

These results are similar to those seen with the E. coli AdhE enzyme which uses ethanol, 1-propanol, and 1-butanol as a substrate, but does not used methanol or secondary or branched chain alcohols. The $K_m$ value obtained for the recombinant EhADH2 enzyme for ethanol (85 mM) is essentially identical to that reported for the native EhADH2 enzyme (80 mM) (11), as were the $K_m$ values for AND$^+$ and NADH, while the $K_m$ value for acetaldehyde was somewhat higher than that reported for native enzyme (0.15 mM) (11).

The $K_m$ for the E. coli AdhE enzyme for ethanol is 30 mM. Measurements of ALDH activity confirmed the identity in substrate specificity between the recombinant and native EhADH2 enzymes, as $K_m$ values for acetyl-Co-A and NADH were essentially identical between the recombinant and native enzymes (11).

Screening For Compounds With Anti-EhADH2 Activity Using E. Coli SHH31 transformed with pMON/EhADH2

The successful complementation of the ΔadhE E. coli strain SHH31 by EhADH2, and the demonstration that the recombinant EhADH2 enzymes substrate specificity appears identical to the native EhADH2 enzyme, provided a useful system for the rapid screening of compounds to identify those capable of inhibiting EhADH2. In this protocol compounds can first be administered to E. coli SHH31 expressing EhADH2, and the effect of the compound on both aerobic and anaerobic growth of the bacteria measured. Compounds which specifically inhibit EhADH2 should inhibit anaerobic growth of SHH31/pMON/EhADH2, but should not significantly alter aerobic growth of this strain.

Compounds with inhibitory activity on anaerobic bacterial growth can then be screened for their effects on amebic growth, and for their ability to inhibit the recombinant EhADH2 enzyme.

To determine whether such a screening system was feasible, an illustrative study was performed by using the compound pyrazole, which is known to be a potent inhibitor of AND$^+$-dependent alcohol dehydrogenases (23). As shown in FIG. 4, pyrazole in a dose-dependent manner significantly inhibited the anaerobic growth of SHH31/pMON/EhADH2, but had a much reduced effect on SHH31/pMON growing under aerobic conditions.

It was then examined whether pyrazole could inhibit the growth of E. histolytica trophozoites. As shown in FIG. 5, pyrazole, at a concentration of 20 to 40 mM significantly inhibited amebic growth. Finally, the $K_i$ of pyrazole for the recombinant EhADH2 molecule was measured and found to be 7.24 mM.

TABLE 1

Comparison of the NAD$^+$ dependent ADH and ALDH activities in the crude lysates of E. coli expressing EhADH2 and control strains.

| E. coli strains | ADH | ALDH |
| --- | --- | --- |
| BL21 (DE3) with pET/EhADH2 | 524 | 90 |
| SHH31 (DE3) with pET/EhADH2 | 417 | 72 |
| SHH31 with pMON/EhADH2 | 82 | 14 |
| BL21 (DE3) (control) | ND | ND |
| SHH31 (control) | ND | ND |

Values are represented as milliunit (mU)/mg. A unit (U) of enzyme activity is defined as a micromole of product formed per minute of incubation.
*ND: not detectable.

TABLE 2

Enzyme activities and $K_m$ values of the purified recombinant EhADH2.

| Reactions | $K_{cat}$ (mol substrate/ mol of enzyme/min) | | $K_m$ (mM) |
| --- | --- | --- | --- |
| acetaldehyde + NADH | 854 | acetaldehyde | 2.9 |
| | | NADH | 0.28 |
| acetyl-CoA + NADH | 154 | acetyl-CoA | 0.04 |
| | | NADH | 0.17 |
| ethanol + NAD$^+$ | 461 | ethanol | 85 |
| | | NAD$^+$ | 0.55 |
| 1-propanol + NAD$^+$ | 326 | 1-propanol | 40 |
| | | NAD$^+$ | 0.25 |

Various other examples will be apparent to the person skilled in the art after reading the present disclosure without departing from the spirit and scope of the invention. It is intended that all such other examples be included within the scope of the claims appended hereto.

References

1. Stanley, S. L., Jr. (1993) in *Conn's Current Therapy*, ed. Rakel, R. E. (Saunders, Philadelphia) 45:60–62.

2. Lawford, R. & Sorrell, T. C. (1994) *Clin. Infect. Dis.* 19, 346–348.

3. Johnson, P. J. (1993) *Parasitol. Today* 9, 183–186.

4. Grogl, M., Martin, R. K., Oduola, A. M. J., Milhous, W. K. & Kyle, D. E. (1991) *Am. J. Trop. Med. Hyg.* 45, 98–111.

5. Lossick, J. G., Muller, M. & Gorrell, T. E. (1986) *J. Infect. Dis.* 153, 948–955.

6. Townson, S. M., Laqua, H., Upcroft, P., Boreham, P. F. L. & Upcroft, J. A. (1992) *Trans. R. Soc. Trop. Med. Hyg.* 86, 521–522.

7. Upcroft, J. A. & Upcroft, P. (1993) *Parasitol. Today* 9, 187–190.

8. Reeves, R. E. (1984) *Adv. Parasitol.* 23, 105–142.

9. Lo, H. & Reeves, R. E. (1978) *Biochem. J.* 171, 225–230.

10. Yang, W., Li, E., Kairong, T. & Stanley, S. L., Jr. (1994) *Motl. Biochem. Parasitol.* 64, 253–260.

11. Bruchhaus, I. & Tannich, E. (1994) *Biochem. J.* 303, 743–748.

12. Goodlove, P. E., Cunningham, P. R., Parker, J. & Clark, D. P. (1989) *Gene* 85, 209–214.

13. Nair, R. V., Bennett, G. N. & Papoutsakis, E. T. (1994) *J. Bacteriol.* 176, 871–885.

14. Fischer, R. J., Helms, J. & Durre, P. (1993) *J. Bacteriol.* 175, 6959–6969.

15. Gupta, S. & Clark, D. P. (1989) *J. Bacteriol.* 171, 3650–3655.

16. Winkelman, J. W. & Clark, D. P. (1986) *J. Bacteriol.* 167, 362–367.

17. Diamond, L. S., Harlow, D. R. & Cunnick, C. C. (1978) *Trans. R. Soc. Trop. Med. Hyg.* 72, 431–432.

18. Studier, F. W., Rosenberg, A. H., Dunn, J. J. & Dubendorff, J. W. (1990) *Methods Enzymol.* 185, 60–89.

19. Li, E., Locke, B., Yang, N. C., Ong, D. E. & Gordon, J. I. (1987) *J Biol Chem* 262, 13773–13779.

20. Stanley, S. L., Jr., Becker, A., Kunz-Jenkins, C., Foster, L. & Li, E. (1990) *Proc. Natl. Acad. Sci. USA* 87, 4976–4980.

21. Kessler, D., Leibrecht, I. & Knappe, J. (1991) *FEBS Lett.* 281, 59–63.

22. Guan, K. & Dixon, J. E. (1991) *Anal. Biochem.* 192, 262–267.

23. Li, T. K. & Theorell, H. (1969) *Acta Chem. Scand.* 23, 892–902.

24. Leonardo, M. R., Cunningham, P. R. & Clark, D. P. (1993) *J. Bacteriol.* 175, 870–878.

25. Flores, B. M., Stanley, S. L., Jr., Yong, T., Ali, M., Yang, W., Diedrich, D. L. & Torian, B. E. (1995) *J. Infect. Dis.* In press.

26. Kumar, A., Shen, P. S., Descoteaux, S., Pohl, J., Bailey, G. & Samuelson, J. (1992) *Proc. Natl. Acad. Sci. USA* 89, 10188–10192.

What is claimed is:

1. A method of screening agents for the capability to inhibit EhADH2 enzyme activity comprising:

(a) culturing under anaerobic cell culture conditions an *E. coli* cell mutant carrying a deletion of the adhE gene complemented by the *E. histolytica* EhADH2 gene whereby said *E. coli* cell mutant expresses EhADH2 protein, (b) combining a predetermined quantity of the agent to be tested with the cell culture, (c) monitoring the combination to determine the inhibitory effect upon anaerobic growth of the *E. coli* cell mutant and compared with a control cultured under aerobic conditions, and (d) wherein inhibition of anaerobic growth indicates that said agent is capable of inhibiting EhADH2 enzyme activity.

2. The method of claim 1 in which the inhibition is monitored by spectrophotometrically determining the optical density of the cell culture at 600 nm.

3. An *E. coli* cell mutant carrying a deletion of the adhE gene complemented by the *E. histolytic* EhADH2 gene and designated *E. coli*/EhADH2.

* * * * *

UNITED STATES PATENT AND TRADEMARK OFFICE
CERTIFICATE OF CORRECTION

PATENT NO. : 5,807,700
DATED      : September 15, 1998
INVENTOR(S) : Samuel L. Stanely, Jr.

It is certified that error appears in the above-identified patent and that said Letters Patent is hereby corrected as shown below:

On the title page, item [75] Inventor: should read --Samuel L. Stanley, Jr.--

Signed and Sealed this

Seventeenth Day of August, 1999

Attest:

Q. TODD DICKINSON

Attesting Officer

Acting Commissioner of Patents and Trademarks